(12) United States Patent
Palleschi et al.

(10) Patent No.: US 8,309,362 B2
(45) Date of Patent: Nov. 13, 2012

(54) PROCESS FOR THE PREPARATION OF MODIFIED ELECTRODES, ELECTRODES PREPARED WITH SAID PROCESS, AND ENZYMATIC BIOSENSORS COMPRISING SAID ELECTRODES

(75) Inventors: Giuseppe Palleschi, Rome (IT); Francesco Ricci, Rome (IT); Danila Moscone, Fondi (IT); Alessandro Poscia, Rignano Sull'Arno (IT)

(73) Assignee: A. Menarini Industrie Farmaceutiche Riunite S.R.L., Firenze (IT)

(*) Notice: Subject to any disclaimer, the term of this patent is extended or adjusted under 35 U.S.C. 154(b) by 764 days.

(21) Appl. No.: 12/002,168

(22) Filed: Dec. 13, 2007

(65) Prior Publication Data
US 2008/0160625 A1 Jul. 3, 2008

(30) Foreign Application Priority Data
Dec. 13, 2006 (IT) ................................ FI2006A0322

(51) Int. Cl.
*G01N 27/26* (2006.01)

(52) U.S. Cl. ................ 436/95; 422/400; 204/403.01; 204/403.12; 204/403.14; 204/412; 205/777.5; 435/287.9; 600/347

(58) Field of Classification Search .............. 436/95; 422/400; 435/287.9; 600/347; 204/403.01, 204/403.12, 403.14, 412; 205/777.5
See application file for complete search history.

(56) References Cited

U.S. PATENT DOCUMENTS

| 4,652,530 | A * | 3/1987 | Rothman et al. ............... 436/92 |
| 4,859,306 | A * | 8/1989 | Siddiqi et al. ............... 204/416 |
| 5,876,581 | A | 3/1999 | Itaya et al. |
| 2004/0045821 | A1* | 3/2004 | Cui et al. ............... 204/403.02 |
| 2004/0140209 | A1* | 7/2004 | Choi et al. ............... 204/403.01 |
| 2006/0216704 | A1* | 9/2006 | Newton et al. ............... 435/5 |
| 2010/0000882 | A1* | 1/2010 | Wang et al. ............... 205/781 |

OTHER PUBLICATIONS

R. Vittal et al., Advances in Colloid and Interface Science, 2006, vol. 119, pp. 55-68.*

* cited by examiner

*Primary Examiner* — In Suk Bullock
*Assistant Examiner* — Timothy G Kingan
(74) *Attorney, Agent, or Firm* — Abelman, Frayne & Schwab

(57) ABSTRACT

A process is described for the preparation of modified electrodes useful for the measurement of analytes in biological fluids, comprising the deposition of Prussian blue on screen printed electrodes, and the modified electrodes prepared via said process; the enzymatic electrodes and the biosensors comprising said modified electrodes and the method for the determination of analytes in biological fluids which uses said modified electrodes are also described.

14 Claims, 4 Drawing Sheets

PROCESS FOR THE PREPARATION OF MODIFIED ELECTRODES, ELECTRODES PREPARED WITH SAID PROCESS, AND ENZYMATIC BIOSENSORS COMPRISING SAID ELECTRODES

FIELD OF THE INVENTION

The present invention refers to the field of modified electrodes for the measurement of analytes in biological fluids, and in particular a new process for the preparation of electrodes modified with Prussian blue, modified electrodes prepared as described, biosensors comprising said electrodes and the method for the determination of analytes in biological fluids using said electrodes.

STATE OF THE ART

The use of Prussian blue to modify amperometric enzymatic electrodes has been known for some time, and resulted from the discovery, going back to the 80s, that Prussian blue can be deposited in layers on electrodes of different materials such as platinum, vitreous carbon, $SnO_2$ and $TiO_2$, and has a catalytic effect in reduction of the hydrogen peroxide produced during the enzymatic oxidisation of the analyte.

With said electrodes modified with Prussian blue, the concentration of hydrogen peroxide formed can be identified, thus permitting indirect measurement of the concentration of the oxidised analyte, which is directly proportional to the quantity of hydrogen peroxide produced.

These electrodes modified with Prussian blue have therefore been used for analytical applications, in particular in amperometric biosensors for the measurement of glucose levels in the blood. In addition to acting as an electrochemical mediator in reduction of the hydrogen peroxide, the layer of Prussian blue can also be used as a substrate for immobilisation of the oxidase enzyme.

The electrodes modified with Prussian blue can be prepared for example by means of electrochemical deposition of solutions of ferric ferrocyanide on an electrode consisting of one of the above-mentioned materials. The U.S. Pat. No. 5,876,581, for example, describes an electrochemical deposition process in which a pair of electrodes are immersed in a solution containing the Iron (III) and hexacyanoferrate (III) ions; performing electrolysis with one of the two electrodes as cathode and the other as anode, a layer of insoluble ferric hexacyanoferrate (III), known as Prussian blue, deposits on the surface of the cathode.

The electrodes that can be used in this process according to U.S. Pat. No. 5,876,581 require the presence of a cathode made of or coated in an inert metal such as platinum, rhodium, gold etc. or an oxide of a conductive metal or a semi-conductor.

More recently these traditional electrodes have been superseded by screen printed electrodes (SPEs), which have numerous advantages: they are inexpensive, easy to prepare, they are versatile and suitable for large-scale industrial production.

As mentioned above, electrodes modified with Prussian blue have been used for some time now, depositing this product on the surface of the electrode by means of electrochemical techniques. Said techniques, however, are not suitable for the large-scale production of modified electrodes starting from screen printed electrodes for two main reasons:
1) the electrochemical procedures are generally long, and have to be performed electrode by electrode, with an enormous waste of time in the case of preparation of a large number of electrodes; and 2) the flat shape of the screen printed electrodes makes use of the electrochemical procedures difficult and laborious since the latter require immersion of the electrode in the solution containing the ionic species, and this can lead to the formation of a layer of Prussian blue also on the surface of the reference electrode, obstructing electrical conductivity and preventing use of the screen printed electrode for analytical purposes.

For these reasons, as far as the Applicant is aware, electrochemical procedures for deposition of Prussian blue on screen printed electrodes do not currently exist. A process for chemical deposition of Prussian blue on a screen printed electrode is described by Ricci et al. in *Biosensors and Bioelectronics* 18 (2003) 165-174. Said process comprises, prior to chemical deposition of the Prussian blue, electrochemical pre-treatment of the electrodes, which are electrochemically treated for 3 minutes at a potential of 1.7 V. According to this article, said procedure is essential for obtaining improved reproducibility and response of the electrode, but on the other hand makes production of the modified electrodes very laborious, requiring electrochemical pre-treatment for each of them and thus nullifying the advantages of the chemical deposition.

In the process described in the above article, furthermore, the Prussian blue is deposited on the electrode manually, by means of a complicated procedure which requires great caution in order to prevent an increase in the internal resistance of the system: a mixture must be prepared on the spot, adding a solution of potassium ferricyanide in HCl to a solution of ferric chloride in HCl, after which a drop of said mixture is deposited exclusively on the surface of the working electrode, trying to avoid the reference electrode and the counter-electrode.

Even with the above precautions, the electrodes modified in this way are limited in terms of reproducibility of the deposition and stability of the layer of Prussian blue; therefore, even though the screen printed electrodes are in themselves characterised by a high level of reproducibility of the electrode surface, responsible for the stability and reproducibility of the electric signal of the analyte, the poor reproducibility and lack of uniformity in preparation of the layer of Prussian blue creates serious problems in measurement of the quantity of analytes in the biological fluids, and in general in the applications for which the electrode is intended.

Given the advantages connected with the use of screen printed electrodes, it is evident that there is a great need in the sector for an easily scalable process, via which the surface of electrodes screen printed with Prussian blue can be modified, overcoming the drawbacks highlighted above for the known processes.

SUMMARY OF THE INVENTION

The Applicant has developed a new process, particularly inexpensive and simple to produce, which permits modification of screen printed electrodes with Prussian blue, obtaining electrodes with a high level of stability and reproducibility, useful in the production of planar biosensors for the quantitative determination of analytes in biological fluids.

The object of the present invention is therefore a process for the preparation of a screen printed electrode modified with Prussian blue, characterised in that it comprises sequential deposition on the surface of said screen printed electrode of a solution comprising the Iron (III) or Iron (II) ion and at least one surface-active agent in an appropriate solvent and a solution comprising the ferrocyanide (II) or ferricyanide (III) ion and at least one surface-active agent in an appropriate solvent, said solutions having concentrations such as to obtain the formation of Prussian blue directly on the surface of the electrode.

The screen printed electrode modified with Prussian blue prepared by means of the above-mentioned process, the enzymatic electrode and the enzymatic biosensor which comprise said electrode, and a method for determination of the quantity of an analyte in a biological sample comprising contact between said sample and the above-mentioned enzymatic biosensor constitute a further subject of the invention.

Characteristics and advantages of the invention will be illustrated in detail in the following description.

DETAILED DESCRIPTION OF THE INVENTION

Figure 1:
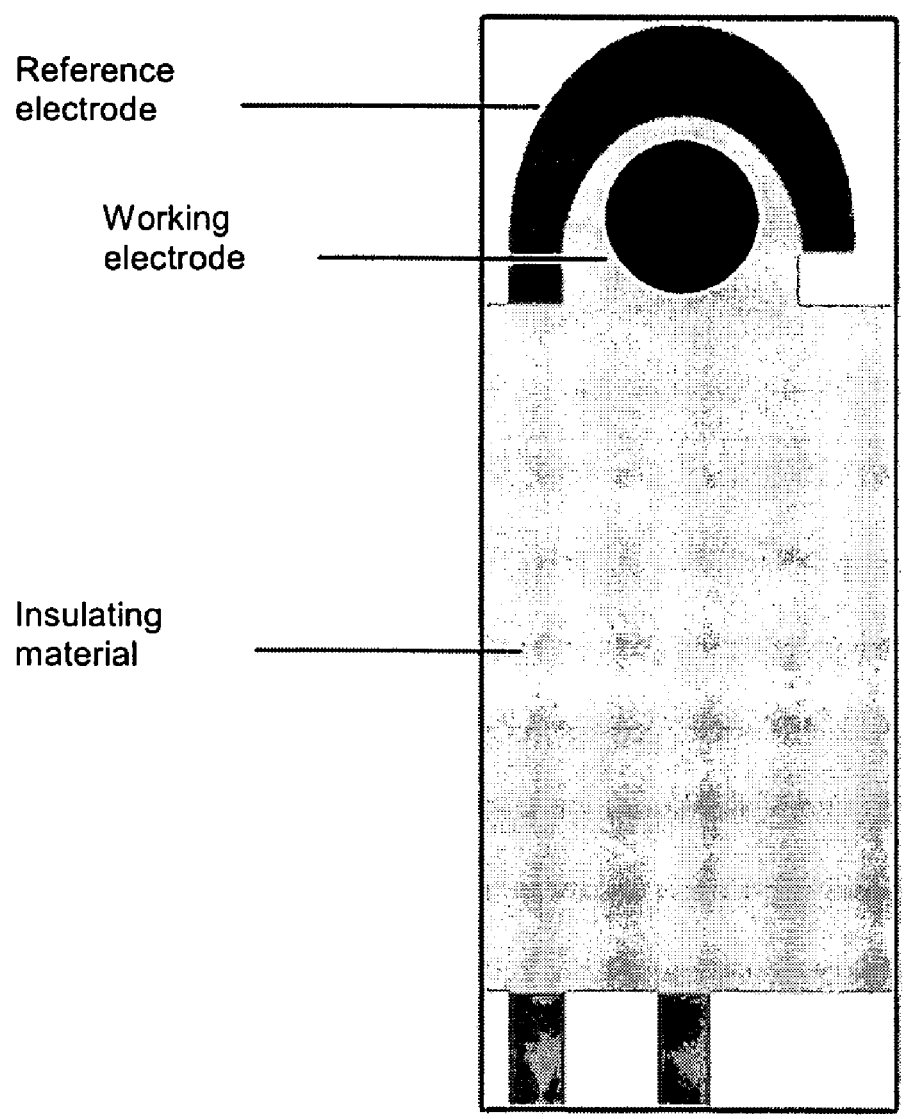
FIG. 1: Profile of the modified screen printed electrode prepared as described in Example 1.

The solution containing the Iron (III) or Iron (II) ion used in the process of the invention is for example an acid solution with pH between 0.5 and 6.0, preferably an acid solution obtained by addition of HCl, of a compound chosen from the group consisting of Iron (III) or Iron (II) salts of inorganic acids, for example ferric chloride, ferric sulphate and ferric nitrate; preferably the present solution is a solution of ferric chloride in aqueous HCl 0.01 M having pH 2.0.

The concentration of the Iron (III) or Iron (II) ion in the above-mentioned solution can be for example between 20 mM and 2 M, and is preferably 1 M.

The solution containing the hexacyanoferrate (III) ion according to the invention is for example an acid solution with pH between pH 0.5 and 6.0, obtained preferably by addition of HCl, of a salt containing the ferrocyanide $Fe(CN)_6^{4-}$ ion or ferricyanide $Fe(CN)_6^{3-}$ ion, for example sodium, potassium, ammonium or cobalt hexacyanoferrate; preferably the present solution is a solution of potassium ferricyanide $K_3Fe(CN)_6$ in aqueous HCl 0.01 M having pH 2.0.

The concentration of the Ferrocyanide (II) or Ferricyanide (III) ion in the above-mentioned solution can be for example between 20 mM and 2 M, and is preferably 1M.

According to the invention, the present process comprises deposition of the solution containing the Iron (III) or Iron (II) ion on the surface of the working electrode and, immediately after, deposition of the solution containing the hexacyanoferrate (III) ion, in equal volume and concentration.

The volume of the two solutions with concentration between 20 mM and 2 mM is for example between 100 nL and 4 µL for an electrode surface of between 0.314 $mm^2$ and 3.14 $cm^2$, preferably 3.14 $mm^2$.

Electrodes screen printed on inert material, for example polycarbonate, polyester, polyvinylchloride (PVC) or other plastic material, with suitable inks of conductive materials, for example graphite, silver, gold or platinum, are suitable for use in the present process for preparing the modified electrodes of the invention; graphite ink is preferred for the working electrode.

After mixing the two solutions, the mixture is left to rest for a period, for example, of between 2 minutes and 2 hours, and preferably 10 minutes; the working electrode surface is then washed with a washing solution consisting, for example, of an acid aqueous solution with pH between 0.5 and 6.0, and preferably an aqueous solution of HCl 0.01 M having pH 2.0.

Following this, the working electrode can be further washed with distilled water. The electrodes thus modified are then left to dry in a stove for example at a temperature between 50° C. and 200° C. for a period of between 10 minutes and 3 hours. Preferably the electrode is placed in a stove at a temperature of 100° C. for 1 hour 30 minutes.

The two solutions comprising the Iron (III) or Iron (II) ion and the ferrocyanide (II) or ferricyanide (III) ion according to the invention furthermore comprise at least one surface-active agent, chosen from cationic, anionic, amphoteric surface-active agents and their mixtures, in quantities for each solution, for example, of between 0.001 and 10% in weight with respect to the total volume of the solution. Preferably the surface-active agent is chosen from the group consisting of sodium lauryl sulphate and lauryl ethoxy sulphate, benzalkonium chloride, compounds belonging to the family of products known under the trade name Tween®, i.e. polyoxyethylene derivatives of esters of fatty acids with sorbitol, and their mixtures.

According to a particularly preferred embodiment of the invention, the surface-active agent polyoxyethylene (20) sorbitan monolaurate, sold under the name Tween® 20 is added to each of the two solutions comprising respectively the Iron (III) or Iron (II) ion and the ferrocyanide (II) or ferricyanide (III) ion, in quantities of 0.05% in weight with respect to the total volume of the solution.

With the present deposition procedure, a layer of Prussian blue can be obtained on the surface of the working electrode which is extremely reproducible and active from the electrochemical point of view. Furthermore, with the cyclic voltammetry technique, the quantity of Prussian blue present on the working electrode following the deposition has been determined, identifying values of between 10 and 200 $nmol/cm^2$ and preferably 100 $nmol/cm^2$.

With the present process, therefore, a massive deposition of Prussian blue can be obtained, never observed previously with either chemical or electrochemical processes; the high surface density of the Prussian blue present on the surface of the electrode allows extremely high operative stability to be obtained without affecting the catalytic activity of the Prussian blue vis-à-vis reduction of the $H_2O_2$. The electrodes modified with Prussian blue prepared with the process of the invention can be used for the preparation of enzymatic biosensors with both two and three electrodes, which are also the subject of the present invention. In said biosensors, the modified electrode is used as a support for immobilisation of a suitable enzyme, chosen on the basis of the type of analytical determination for which the biosensor is intended, i.e. such that the analyte to be detected functions as a substrate for the enzyme, generating a product that can be oxidised or reduced electrochemically on the modified electrode, varying the quantity of current detected in proportion to the quantity of analyte present in the fluid analysed.

The present biosensor comprises an enzymatic electrode, i.e. the modified electrode of the invention as described above, on which the enzyme has been immobilised by means of procedures commonly used and known to any expert in the sector, and a cell for receiving the biological fluid to be analysed, so that the latter can come into contact with the enzyme.

According to a preferred embodiment of the invention, the present biosensor comprises a modified electrode of the invention on which the glucose oxidase enzyme has been immobilised, and is used for determination of the glucose in biological fluids such as blood, serum or plasma; in this case the analyte is the glucose which, oxidised by the enzyme, produces $H_2O_2$ which is reduced on the modified electrode due to the potential applied between this electrode and the reference electrode, generating a current signal proportional to the quantity of $H_2O_2$ produced and therefore to the quantity of glucose present in the fluid contained in the cell.

A further subject of the invention is the method for determination of the quantity of an analyte in a biological fluid, comprising the application of an appropriate potential value between a modified electrode of the invention as described above and the reference electrode contained in the present biosensor, and reading of the generated current signal.

Preferably, the present method is used for determination of the quantity of glucose on biological fluids and the potential applied is low, for example between −250 mV and +200 mV, preferably −50 mV.

The present process for the preparation of electrodes modified with Prussian blue, as described above, has a high level of reproducibility of the deposition stage, which positively affects reproducibility of the measurement performed with the electrodes modified via this process; furthermore, it provides a modified electrode with greater operative stability than any electrode modified with Prussian blue prepared so far with the known processes. It has been observed that in the electrodes modified by means of the present process, the layer of Prussian blue is still active and presents a reduction in its electrochemical activity of only approximately 35%, after 150 hours of continuous use.

In addition to greater operative stability, the electrodes modified with Prussian blue prepared with the process of the invention also have greater long-term stability during storage.

These stability values, both operative and storage, and reproducibility values, in the case of biosensors with both two and three electrodes, are furthermore achieved by a process which does not require, contrary for example to the process described by Ricci et al. in *Biosensors and Bioelectronics* 18 (2003) 165-174, electrochemical pre-treatment of the electrode before deposition of the Prussian blue, and is therefore much less laborious and easy to automate, and therefore scalable at industrial level.

A further advantage of the modified electrodes of the invention, in the case of biosensors with two electrodes which can be used, for example, for determination of the glucose, is that of comprising a working electrode and a reference electrode, while they do not require the counter-electrode, contrary for example to the electrodes modified with Prussian blue described in the above-mentioned article by Ricci et al.

The following examples provide a non-limiting illustration of the invention.

EXAMPLE 1

Preparation of the Modified Electrode

Following the known procedure, a screen printed electrode was prepared on a polyester sheet, comprising a circular-shaped working electrode with diameter of 2 mm prepared with a graphite ink and a silver reference electrode; the surface of the working electrode is delimited by an ink made of insulating material. FIG. 1 shows the profile of the electrode obtained in this way.

The following two solutions were then prepared: 1) 1 M solution of potassium ferricyanide $K_3Fe(CN)_6$ in HCl 10 mM and 2) 1 M solution of ferric chloride in HCl 10 mM. Tween® 20 was added to each of the two solutions in a quantity of 0.05% in weight with respect to the total volume of the solution.

With an automatic dispensing machine, 1 μl of the solution 1) was deposited on the surface of the working electrode and, immediately after, with the same automatic dispensing technique, 1 μl of the solution 2) was deposited on the same surface of the working electrode, thus resulting in 2 μl of a solution of ferric chloride and potassium hexacyanoferrate on said surface.

After 10 minutes, the electrodes thus modified were washed with a few millilitres of a 10 mM solution of HCl, then placed in a stove at 100° C. for 1 hour.

The procedure described above resulted in deposition on the electrode of an extremely compact and stable layer of Prussian blue, with a high surface density of the Prussian blue on the working electrode.

Figure 2:
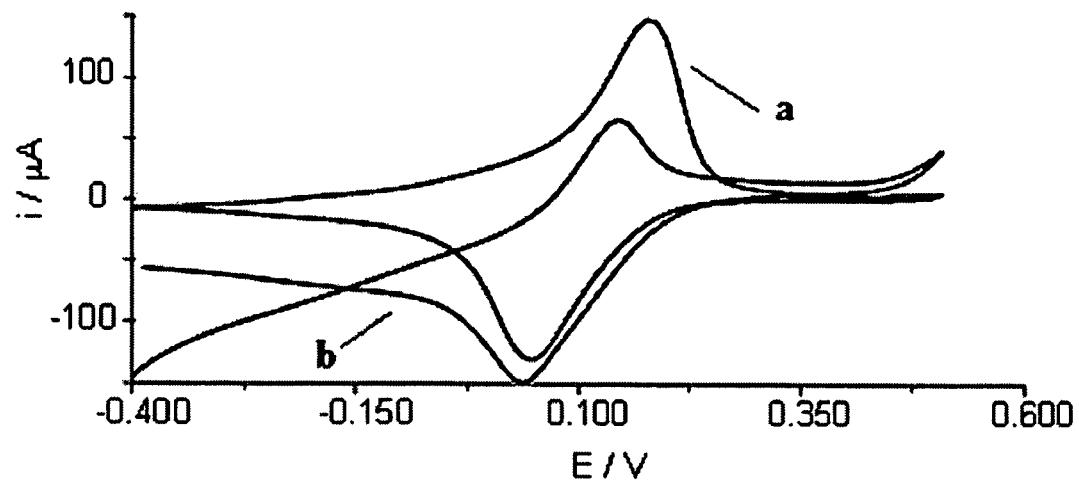
FIG. 2: Cyclic voltammogram recorded using the modified screen printed electrode as described in Example 1 (curve a), and cyclic voltammogram recorded with the same electrode in the presence of $H_2O_2$ (curve b), which shows the electrocatalytic activity of the Prussian blue.

The latter is confirmed by the results of the cyclic voltammetry shown in FIG. 2, which permitted calculation of the quantity of Prussian blue on the surface of the working electrode: the surface density value measured is approximately 100 nmol/cm$^2$, much greater than reported in the literature so far using different deposition techniques.

EXAMPLE 2

Determination of the Catalytic Activity of Prussian Blue for the Electrode Prepared in Example 1

The properties of the modified electrode prepared as described above in Example 1 were verified by means of cyclic voltammetry, in the potential range −0.4 to 0.4 V.

FIG. 2 shows the voltammograms obtained for the screen printed electrode not yet modified and for the same electrode modified with Prussian blue, prepared as described above in Example 1. For the latter electrode, the increase in the cathodic wave to approximately 0.05 V in the presence of hydrogen peroxide can be seen in the voltammogram, showing the catalytic activity of the layer of Prussian blue deposited on the electrode.

EXAMPLE 3 (COMPARISON)

Preparation of the Modified Electrode as Described by Ricci et al. in *Biosensors and Bioelectronics* 18 (2003) 165-174

Following the procedure described previously in the article by Ricci et al., *Biosensors and Bioelectronics* 18 (2003) 165-174, an electrode screen printed on a polyester sheet, comprising a circular shaped working electrode with diameter of 2 mm prepared with a graphite ink and a silver reference electrode, was modified; the surface of the working electrode is delimited by an ink made of insulating material.

The following two solutions were then prepared: 1) 0.1 M solution of potassium ferricyanide $K_3Fe(CN)_6$ in HCl 10 mM and 2) 0.1 M solution of ferric chloride in HCl 10 mM.

Before deposition of the two solutions by means of the electrochemical method, a procedure unsuitable for automation and much more laborious and longer than that of Example 1, the electrode was pre-treated by application of a constant potential equal to 1.7 V vs. Ag/AgCl for 3 minutes.

Using an automatic dispensing machine, 20 μl of the solution 1) were deposited on the surface of the working electrode and, immediately after, using the same deposition technique, 20 μl of the solution 2) were deposited on the same surface of the working electrode, thus obtaining 40 μl of a mixture of ferric chloride and potassium hexacyanoferrate.

Figure 3:
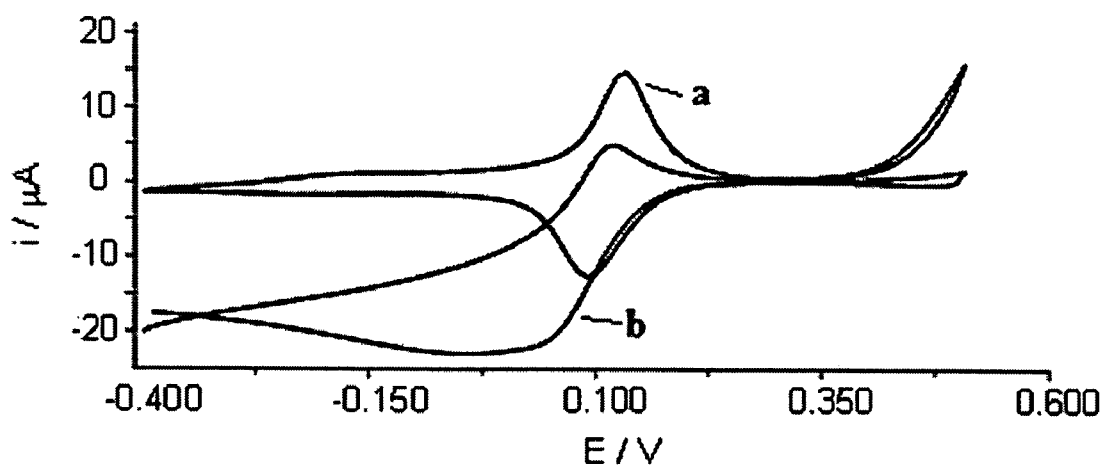
FIG. 3: Cyclic voltammogram recorded using the modified screen printed electrode as described in Example 3 for comparison (curve a), and cyclic voltammogram recorded with the same electrode in the presence of $H_2O_2$ (curve b), which shows the electrocatalytic activity of the Prussian blue.

After 10 minutes, the electrodes thus modified were washed in a few millilitres of a 10 mM solution of HCl, then placed in a stove at 100° C. for 1 hour. The electrocatalytic activity of the layer of Prussian blue thus deposited was assessed following the same procedure as the one described in Example 2. FIG. 3 shows the cyclic voltammograms obtained for the modified screen printed electrode as described above.

EXAMPLE 4

Determination of the Analytical Performances of the Modified Electrodes According to the Invention and According to the Prior Art The analytical performances of the electrodes modified with Prussian blue prepared as described above in Examples 1 and 3 were tested considering the response to $H_2O_2$, the operative and non-operative stability and the reproducibility. As regards reproducibility, the reproducibility values, calculated as Relative Standard Deviation percentage (abbreviated below to RSD %), for the modified electrode as described in Example 3 are approximately 20%, incompatible with any industrial type of application, whereas an RSD % of 5% was calculated for the electrode of the invention, modified as described in Example 1.

Figure 4:
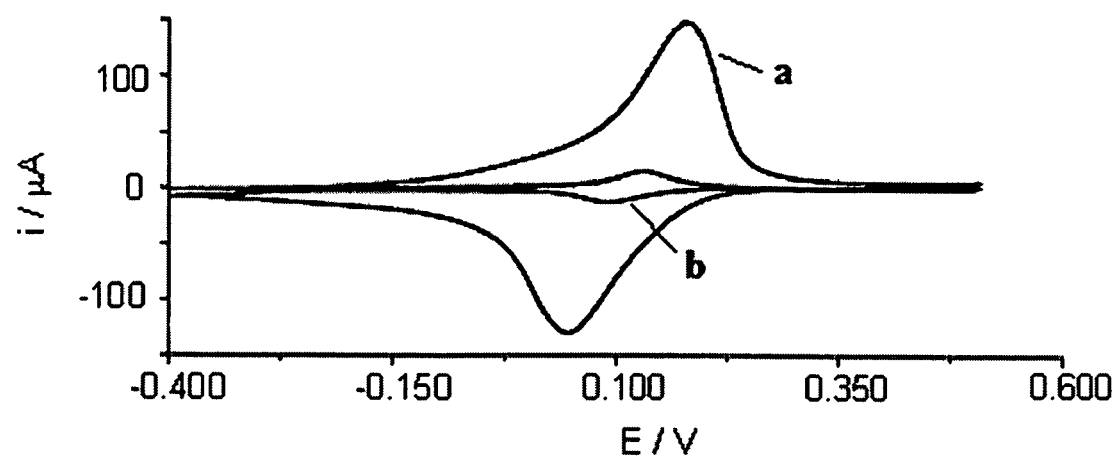
FIG. 4: Comparison between cyclic voltammogram recorded using the modified electrode as described in Example 1 (curve a) and voltammogram recorded with the modified electrode as described in Example 3 for comparison (curve b). Note the greater deposition of Prussian blue obtained with the electrode of Example 1.

As regards the thickness of the Prussian blue deposited on the electrodes, with the procedure of the prior art described in Example 3, a layer of Prussian blue is obtained with a surface density of between 1 and 10 nmol/cm$^2$, therefore much lower than the one obtained for the electrode of the invention of Example 1 (approximately 100 nmol/cm$^2$) as shown by comparison of the cyclic voltammetries (FIG. 4).

Figure 5A:
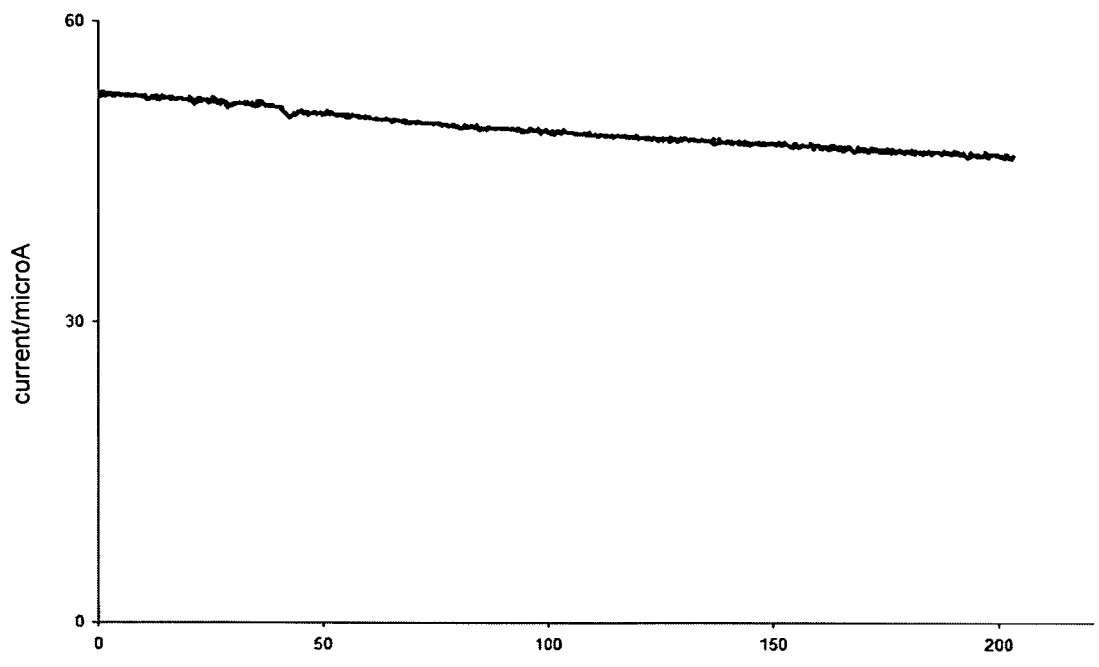
FIG. 5: Comparison between the operative stability of a modified electrode according to Example 1 (FIG. 5a) and a modified electrode according to Example 3 for comparison (FIG. 5b), from which the greater operative stability of the electrode obtained with the procedure described in Example 1 can be noted.
Figure 5B:
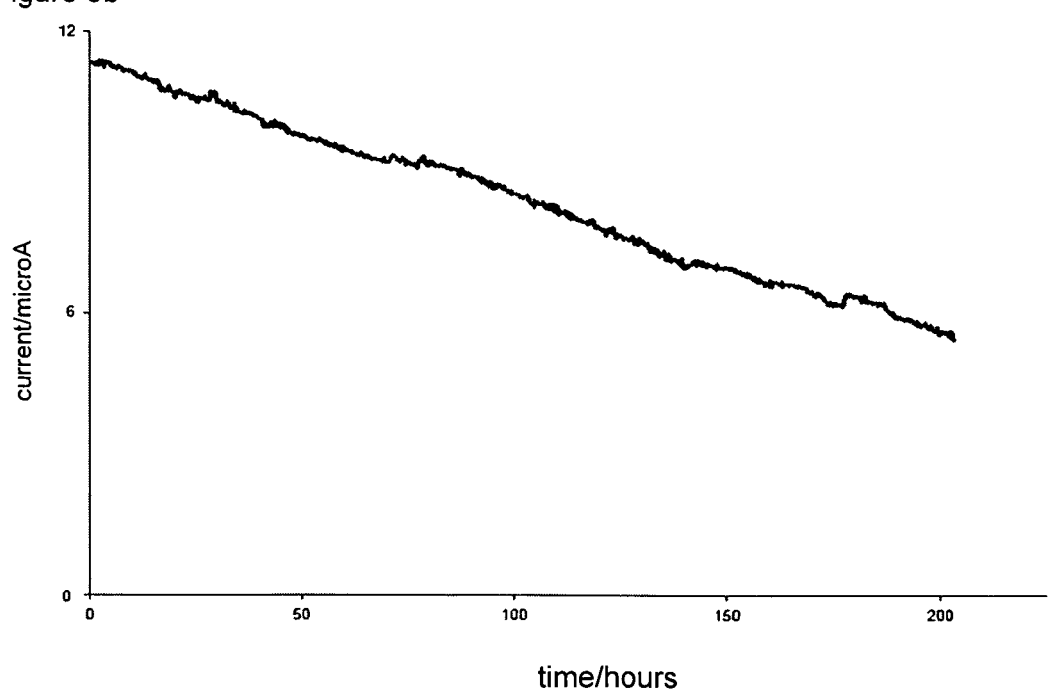

This results in greater operative stability of the Prussian blue, up to a maximum of 200 hours. FIG. 5, for example, shows continuous monitoring with a flow technique, obtained with the two electrodes prepared following the procedures described in Examples 1 and 3. As can be clearly seen, with a 5 mM concentration of $H_2O_2$, both the electrodes provide a reduction current due to the catalytic activity of the Prussian blue, but the electrode of Example 1 shows greater operative stability in the long term, with a reduction in the initial signal of only 20% after 200 hours.

In the case of the electrode of the prior art prepared in Example 3, a more marked reduction is observed equal to approximately 70% after 200 hours.

EXAMPLE 5

Preparation of the Biosensor

The modified electrode prepared as described above in Example 1 was used as a support for immobilisation of the glucose oxidase enzyme, for the purpose of obtaining a biosensor useful for continuous monitoring of glucose in the blood. For this purpose 200 mL of a solution of glutaraldehyde (0.025% v/v in $H_2O$) were deposited on the surface of the working electrode, previously modified with Prussian blue as described above in Example 1. After approximately 25 minutes, 200 nL of a mixture obtained by dissolving 10 mg of the glucose oxidase enzyme in 1 ml of an aqueous solution of Nafion® (0.1%) were deposited on the same surface of the working electrode. Here again, it is left to rest for approximately 25 minutes so as to obtain complete drying of the solution deposited.

The invention claimed is:

1. A process for the preparation of a screen printed electrode modified with Prussian blue, characterised in that it comprises sequential deposition on the working electrode surface of said screen printed electrode of a solution comprising the Iron (III) or Iron (II) ion and at least one surface-active agent in an appropriate solvent and a solution comprising the ferrocyanide (II) or ferricyanide (III) ion and at least one surface-active agent in an appropriate solvent, said solutions having concentrations such as to obtain the formation of Prussian blue directly on the surface of the working electrode; wherein said solutions have equal concentration of between 20 mM and 2 M, and are deposited in equal volume of between 100 nL and 4 μL for an electrode surface between 0.314 mm$^2$ and 3.14 cm$^2$;
  after mixing of the two solutions, the mixture is left to rest for a period of between 2 minutes and 2 hours; the working electrode surface is then washed with a washing solution; the electrode thus modified are left dried at a temperature between 50° C. and 200° C.; and
  wherein said screen printed electrode has not undergone pre-treatment before said sequential deposition of the solutions.

2. The process as claimed in claim 1, wherein said solution comprising the Iron (III) or Iron (II) ion is an acid solution with pH between 0.5 and 6.0 of a compound chosen from the group consisting of Iron (III) or Iron (II) salts of inorganic acids.

3. The process as claimed in claim 2, wherein said Iron (III) or Iron (II) salt of inorganic acids is chosen from ferric chloride, ferric sulphate and ferric nitrate.

4. The process as claimed in claim 2, wherein said solution is a solution of ferric chloride in aqueous HCl 0.01 M having pH 2.0.

5. The process as claimed in claim 1, wherein said solution comprising the hexacyanoferrate (III) ion is an acid solution with pH between pH 0.5 and 6.0 of a salt containing the ferrocyanide (II) or ferricyanide (III) ion.

6. The process as claimed in claim 5, wherein said salt is chosen from sodium, potassium, ammonium and cobalt hexacyanoferrate.

7. The process as claimed in claim 5, wherein said solution is a solution of potassium ferricyanide $K_3Fe(CN)_6$ in aqueous HCl 0.01 M having pH 2.0.

8. The process as claimed in claim 1, wherein said screen printed electrode is made of inert material screen printed with graphite ink.

9. The process as claimed in claim 1, furthermore comprising the stages of leaving the solutions deposited to rest for 10 minutes, washing the surface of the working electrode with a washing solution consisting of an aqueous acid solution with pH between 0.5 and 6.0, washing with distilled water if necessary and leaving to dry in a stove at a temperature between 50° C. and 200° C., for a period of between 10 minutes and 3 hours.

10. The process as claimed in claim 9, wherein said washing solution is an aqueous solution of HCl 0.01 M having pH 2.0.

11. The process as claimed in claim 10, wherein the electrode is left to dry in a stove at a temperature of 100° C. for a period of 1 hour 30 minutes.

12. The process as claimed in claim 1, wherein said surface-active agent is chosen from cationic, anionic, amphoteric surface-active agents and mixtures thereof, and added in quantities for each solution of between 0.001 and 10% in weight with respect to the total volume of the solution.

13. The process as claimed in claim 12, wherein said surface-active agent is chosen from the group consisting of sodium lauryl sulphate and lauryl ethoxy sulphate, benzalkonium chloride, polyoxyethylene derivatives of esters of fatty acids with sorbitol, and mixtures thereof.

14. The process as claimed in claim 13, wherein said surface-active agent is polyoxyethylene (20) sorbitan monolaurate, in a quantity of 0.05% in weight with respect to the total volume of the solution.

* * * * *